(12) United States Patent
Lin (10) Patent No.: US 11,732,235 B1
(45) Date of Patent: Aug. 22, 2023

(54) HIGHLY SCALABLE AND PRACTICAL METHOD FOR IMMOBILIZING AND EFFICIENTLY CULTURING ALGAE FOR VARIOUS APPLICATIONS

(71) Applicant: Mark Lin, Palos Verdes Estates, CA (US)

(72) Inventor: Mark Lin, Palos Verdes Estates, CA (US)

(*) Notice: Subject to any disclaimer, the term of this patent is extended or adjusted under 35 U.S.C. 154(b) by 0 days.

(21) Appl. No.: 18/305,361

(22) Filed: Apr. 23, 2023

(51) Int. Cl.
*C12N 1/12* (2006.01)
*A01G 33/00* (2006.01)
*C12M 1/00* (2006.01)
*C12R 1/89* (2006.01)

(52) U.S. Cl.
CPC .............. *C12N 1/12* (2013.01); *A01G 33/00* (2013.01); *C12M 21/02* (2013.01); *C12M 23/02* (2013.01); *C12R 2001/89* (2021.05)

(58) Field of Classification Search
CPC ...................................................... C12N 1/12
See application file for complete search history.

(56) References Cited

PUBLICATIONS

Yamamoto, "Detection of algal lysing biological agents in lakes by the soft agar overlay technique," Japanese Journal of Limnology 39(1):9-14, 1978.*

* cited by examiner

*Primary Examiner* — Rosanne Kosson
(74) *Attorney, Agent, or Firm* — Metropolis IP Group, LLC; Eric Kang (57) ABSTRACT

A method for preparing a solid medium platform for cultivating algae, comprising obtaining an algae culture solution ("ACS") at approximately room temperature of a specific volumetric quantity, denoted "x"; creating raw agarose solution ("AS") by adding low melting point agarose powder ("AP") to water of a volume equal to "x" in a container that is different from the one used for said ACS; heating and stirring AS; cooling or waiting for the AS to cool down to approximately 15-35% above the gelling temperature of the AS; adding micronutrients supportive of algae growth after AS has cooled to approximately 15-35% above the gelling temperature of the AS to create an agarose micronutrient solution ("AMS"); after the AMS has cooled, combining the AMS with ACS and pouring the mixture into an open container and stirring; apportioning the AMS/ACS mixture into cultivating container(s); and waiting for the mixture to congeal.

10 Claims, 8 Drawing Sheets

A Highly Scalable and Practical Method for Immobilizing and Efficiently Culturing Algae for Various Applications

FIG. 1

TITLE: A Highly Scalable and Practical Method for Immobilizing and Efficiently Culturing Algae for Various Applications

TITLE: A Highly Scalable and Practical Method for Immobilizing and Efficiently Culturing Algae for Various Applications

TITLE: A Highly Scalable and Practical Method for Immobilizing and Efficiently Culturing Algae for Various Applications

FIG. 6

TITLE: A Highly Scalable and Practical Method for Immobilizing and Efficiently Culturing Algae for Various Applications

FIG. 7

TITLE: A Highly Scalable and Practical Method for Immobilizing and Efficiently Culturing Algae for Various Applications

FIG. 8

TITLE: A Highly Scalable and Practical Method for Immobilizing and Efficiently Culturing Algae for Various Applications

HIGHLY SCALABLE AND PRACTICAL METHOD FOR IMMOBILIZING AND EFFICIENTLY CULTURING ALGAE FOR VARIOUS APPLICATIONS

FIELD OF THE INVENTION

The present invention relates to methods for immobilizing and culturing algae in a manner that minimizes the requisite supporting infrastructure.

BACKGROUND OF THE INVENTION

Carbon dioxide from man-made sources is considered to be among the "greenhouse gases" believed to contribute to Earth's climate change trends. Much of this carbon comes from emissions from machines powered by fossil fuels that would have otherwise been "locked" underground and not participating in the atmospheric carbon cycle. The current pressing issue is unless the loading rate of this and other greenhouse gases are dramatically curtailed, dire existential consequences are forecast to transpire during this century.

One segment of the energy community has been developing biofuels from renewable sources, with algae being one such candidate for a number of reasons. For one, algae absorb as much carbon as it releases because that is what it uses for food and therefore their growth is carbon neutral. In particular, *Chlorella vulgaris* ("Cv") is a species of green microalga in the division Chlorophyta, that is not only a dietary supplement or protein-rich food additive and detoxing agent but due to their known ability to produce high levels of lipids [1], is also a good feedstock candidate for biodiesel production.

Sunlight or a suitable light source is one of the essential ingredients in the growth of algae, through a process commonly known as photosynthesis. The byproduct of photosynthesis is oxygen, which is additionally a desirable characteristic for numerous applications.

In fact, research by the National Aeronautical and Space Administration (NASA) has shown potential for the implementation of photobioreactors (PBRs) so that oxygen and harvestable biomass can be produced from algae via photosynthesis [2]. PBRs have many different designs but generally, work by sustaining a closed culture of algae in either a tank or honeycomb structure [3]. In space, a "rack" system has been proposed, with close "shelves" of algae allowing for a large volume to be concentrated within a small area. Exploration into the concept of aerospace travel-sustaining algae cultures is beginning to gain traction, as a system named PBR@LSR (Photobioreactor at the Life Support Rack) was sent to the International Space Station for trial in 2019 [4].

Current PBR technology utilizes a liquid culture medium, which becomes a source of multiple technical challenges, especially due to the complexity of designing a water-based system in zero gravity. Other problems related to liquid medium include uneven distribution of heat and light and nutrients, requiring special designs to optimize absorption and/or methods to "rotate" the algae.

More specifically, problems with algae growth in liquid medium are that in a tubular container, algae closer to the exposed surfaces tend to absorb most of the light while occluding light from reaching algae within the more interior portions of the container. In addition, microalgae, with *Chlorella vulgaris* as a prototype, are unicellular organisms, which tend to "sink" to the bottom of the container when not agitated. Hence, liquid growth systems require a way to agitate or rotate the algae to maintain an even distribution of the microalgae.

Water pumps, agitators, liquid exchange equipment, and pressure valves not only add failure modes but also occupy large portions of space and can reduce process energy efficiency including the well-to-wheel metric if biofuel production is part of the end goal. In the aforementioned photobioreactor system, an unexpected hardware failure led to the termination of the experiment following two weeks of growth [5].

The present invention breaks from the prevailing focus on liquid medium and instead utilizes a solid medium for algae culture, which "immobilizes" the algae and simplifies the requisite mechanical support system requirements compared to those needed for liquid medium culturing platforms. It also circumvents problems associated with growth in liquid, including transportation of liquid in space travel. Solid agar plates have traditionally been used as a way to store and/or culture algae. However, the existing method is "streaking" algae onto the surface of agar plates [6].

By contrast, the present invention incorporates algae into the agar plate by using low melting point agarose, such that algae are incorporated just before the agarose solution solidifies at a temperature that will not kill the algae. In addition, micronutrients are incorporated into the agar plate, so that algae growth can be sustained without the addition of micronutrients for completely closed PBRs. Such a method enables the implementation of relatively simple, compact, production-dense, highly scalable, and potentially robust PBRs for space as well as terrestrial applications.

Solid medium approaches are generally uncommon and none have been found to resemble the present disclosure. The reason for this is there is no real impetus for a solid medium method of algae growth. However, with increasing interest in space travel and ventures, where the costs of infrastructure footprint and complexity are magnified over terrestrial interests, the need for new and innovative approaches based on solid medium growth is commensurately increasing. The development of such an approach can in turn be utilized in terrestrial applications to greatly enhance the efficiency of algae culture in applications such as biofuel production and carbon dioxide sequestration.

Because of the relative lack of past focus on solid medium algae cultivation, certain aspects of optimization have not been adequately scrutinized. While liquid medium algae cultivation has some agitation control parameters (e.g., stirring angular frequency) to optimize, the solid medium has its own unique optimization space that relates to its form factor.

The solid medium form factor is generally defined by the geometry of the agar plate or cultivating container in which the mixture of agarose solution and algae culture congeal. For a given volume, the optimal height of the agar plate is important, wherein the correct height (1) allows immobilized algae even in the "deepest" areas to have minimal "self-shading" effect—this is the fundamental purpose of immobilizing the algae, and (2) takes into consideration limiting factors such as loss of moisture of the agar plate and lighting and space considerations.

Furthermore, for a given volume, if the height of the agar plate or cultivating container is lower, then the wider the base area would be. As the height is reduced for a given base dimension (e.g., radius if the cultivating container has a circular base or edge length(s) for a quadrilateral base), the larger the exposed surface area (the side exposed to gas and light) to volume ratio and potentially higher yield rate of cultivation for a volumetric unit of the solid medium algae due to greater area for carbon dioxide-oxygen gas exchange and incident light. However, the drive to reduce the height is tempered by a much faster agar dry-out rate as well as greater lighting infrastructure demands to assure uniformly sufficient photon exposure across a wider footprint.

Regarding known activity on solid medium growth devoid of any form factor considerations, a paper by Shirai et al. [7] discusses the development of a solid medium for the growth of a species of cyanobacterium that is known to be difficult to culture on agar plates. While cyanobacterium is often known as "blue-green algae", technically it is a group of prokaryotic bacteria, while *Chlorella* species that is the subject of the present invention are eukaryotic organisms belonging to the kingdom Protista. Hence, a fundamental difference between Shirai's effort and the present invention is that one is a bacterial culture medium, while the present invention develops an algae culture medium.

Secondly, Shirai's [7] reference recites its purpose from: "The culturing of cyanobacteria on agar media has been routinely used for maintenance or purification of certain species." Hence, the purpose of Shirai's method is for purification, to isolate an axenic strain of cyanobacteria, since bacteria-free strains are required for physiological, genetic, and taxonomic studies. By contrast, the purpose of the method of the present invention is significantly different since it comprises the production of biomass, lipids for biofuel, and oxygen while mitigating carbon dioxide and is applicable for space, energy, and food industries to name a few.

Thirdly, the method of preparing a solid medium culture is significantly different. The distinctions are that Shirai's method for preparing solid medium agarose solution uses a "base of B-12 or CB medium" with a pH of 9.0 and mixed with gels (chemical grade 1, low-ash agar, low melting temperature agarose) in a manner the reference does not further disclose. The cell culture in liquid was mixed with the agarose solution at a ratio of 0.1 mL per 10 mL of agarose solution and the mixture is then allowed to harden. Shirai also presents an alternative method of hardening the agarose solution (medium) on a petri dish and streaking 0.1 mL of diluted culture over the medium with a bent glass rod.

By contrast, the present invention discloses a vastly different method with specific steps and requirements for the homogeneity of the agarose solution, a temperature threshold for adding micronutrients to the agarose solution, a second temperature threshold with different ratios than Shirai's for mixing the algae culture solution with the agarose solution, and a general guideline on the form factor of the algae in solid medium. Furthermore, the second method of the present invention further extends culturing algae within this solid medium that is not currently practiced nor disclosed by others.

SUMMARY OF THE INVENTION

The present invention is drawn to a highly scalable and practical two-part method for immobilizing and efficiently culturing algae, wherein the first part method comprises steps for preparing a solid medium algae culture conducive toward efficient growth and the second part method comprises steps for culturing the algae using photosynthesis and, for open systems or intermittently open(able) systems, periodically adding micronutrients. The steps for preparing solid medium algae culture comprise the creation of or obtaining an algae culture solution ("ACS") at approximately room temperature or 20° C.; separately creating a raw agarose solution ("AS") in liquid solution form and whose gelling temperature is at or below approximately 30° C.; heating and stirring the AS until homogeneous; cooling the AS until approximately 15-35% above the gelling temperature of the AS; adding micronutrients to the AS to create an agarose micronutrient solution ("AMS"); waiting for the AMS to cool further, and once the AMS is at a temperature where the simple average of the AMS temperature and room temperature ACS is between the lower bound gelling temperature of the AMS and 33° C., combining the AMS and ACS in a container and mixing, apportioning the AMS/ACS mixture into high surface area exposed to gas and light to volume ratio (ESA/V) form, and allowing the mixture to congeal to form algae in solid medium ("AiSM"). The steps for cultivating the AiSM comprise placing the high ESA/V AiSM in a system (e.g., PBR) exposed to carbon dioxide-laden gas and turning on a photon (e.g., light) source; cyclically turning the light(s) off and then on within a twenty-four period; for open systems or intermittently open(able) systems, adding micronutrient solution ("MS") to the AiSM; monitoring growth and comparing against a population density criterion ($\delta$) for harvesting/isolating; and based on the population density criterion, either repeating the nourishment cycle or isolating/harvesting.

BRIEF DESCRIPTION OF THE DRAWINGS

The drawings are provided to facilitate understanding in the detailed description. It should be noted that the drawing figures may be in simplified form and might not be to precise scale. In reference to the disclosure herein, for purposes of convenience and clarity, only directional terms such as top, bottom, left, right, up, down, over, above, below, beneath, rear, front, distal, and proximal are used with respect to the accompanying drawings. Such directional terms should not be construed to limit the scope of the embodiment in any manner. System schematics are not meant to convey an accurate perspective or proportional form, but rather to illustrate the elements that are present in the system in a more visually intuitive manner than a rudimentary block diagram listing. Portions of certain figures are accompanied by icons depicting actions, processes, process states, and items. These icons are meant to efficiently convey information in an impactful and potentially more universal manner. Any ambiguity in an icon's meaning is clarified by content provided in the DETAILED DESCRIPTION OF THE INVENTION and not be construed to limit the scope of the embodiment in any manner. Embodiments of the methods and systems represented in the drawings as block diagrams and flowcharts are illustrations of methods.

FIG. 3 is a block diagram showing the steps to culturing AiSM FIG. 4 compares the carbon dioxide consumption of algae in solid and liquid media platforms within closed PBRs across four experimental trials FIG. 5 shows the percent change in spectrophotometry-based population density of the algae culture in liquid medium for each day range within the two-week experimental period as measured in the 430.4 nm wavelength, which corresponds to pigment absorbance values for chlorophyll a FIG. 6 shows the percent change in spectrophotometry-based population density of the algae culture in solid medium for each day range within the two-week experimental period as measured in the 430.4 nm wavelength, which corresponds to pigment absorbance values for chlorophyll a FIG. 7 shows the percent change in spectrophotometry-based population density of the algae culture in liquid medium for each day range within the two-week experimental period as measured in the 662 nm wavelength, which corresponds to pigment absorbance values for chlorophyll a FIG. 8 shows the percent change in spectrophotometry-based population density of the algae culture in solid medium for each day range within the two-week experimental period as measured in the 662 nm wavelength, which corresponds to pigment absorbance values for chlorophyll a

DETAILED DESCRIPTION OF THE INVENTION

MICRONUTRIENTS: The method for preparing solid medium algae and certain method embodiments of culturing algae within a solid medium requires the use of micronutrients to foster algae growth therein. An example and one that was used for validation can be Algae Research and Supply® "F/2 Media" otherwise referred to as Guillard's F/2 Micronutrient or micronutrients, which is a common and widely used enriched seawater medium designed for growing coastal marine algae, especially diatoms, and uses a half-concentrated version of the original formulation, termed "f Medium" [8]. Table 1 lists the components of the F/2 Media "nutrient solution" [9] and the molar concentration in the final medium.

TABLE 1

Components of the F/2 Nutrient Solution

| Components | Stock Solution | Quantity | Final Molar Concentration |
|---|---|---|---|
| NaNO3 | 75 g/L dH2O* | 1 mL | 8.82e−04 M |
| NaH2PO4 H2O | 5 g/L dH2O* | 1 mL | 3.62e−05 M |
| Na2CO3 | 30 g/L dH2O* | 1 mL | 1.06e−04 M |
| Trace Metal Solution | See Table 2 | 1 mL | — |
| Vitamin Solution | See Table 3 | 0.5 mL | — |

*dH2O = distilled water

The "Trace Metal Solution" was prepared by starting with 950 mL of dH2O, adding the components in Table 2 [9], and bringing the final volume to 1 liter with dH2O. The solution was sterilized using an autoclave. Note that the original medium [8] used ferric sequestrene while the exemplary micronutrient used the substitute Na2EDTA·2H2O and FeCl3·6H2O.

TABLE 2

Trace Metal Solution

| Components | Stock Solution | Quantity | Final Molar Concentration |
|---|---|---|---|
| FeCl3 6(H2O) | — | 3.15 g | 1.17e−05 M |
| Na2(EDTA)2(H2O) | — | 4.36 g | 1.17e−05 M |
| CuSO4 5(H2O) | 9.8 g/L dH2O | 1 mL | 3.93e−08 M |
| Na2MoO4 2(H2O) | 6.3 g/L dH2O | 1 mL | 2.60e−08 M |
| ZnSO4 7(H2O) | 22.0 g/L dH2O | 1 mL | 7.65e−08 M |
| CoCl2 6(H2O) | 10.0 g/L dH2O | 1 mL | 4.20e−08 M |
| MnCl2 4(H2O) | 180.0 g/L dH2O | 1 mL | 9.10e−07 M |

The "Vitamin Solution" is prepared by beginning with 950 mL of dH2O, dissolving the thiamine, adding the amounts of the primary stocks as indicated in the quantity columns below in Table 3 [9], and bringing the final volume to 1 liter with dH2O. Then autoclave to sterilize and store in a refrigerator or freezer.

TABLE 3

Vitamin Solution

| Components | Stock Solution | Quantity | Final Molar Concentration |
|---|---|---|---|
| Thiamine HCl (Vitamin B1) | | 200 mg | 2.96e−07 M |
| Biotin (Vitamin H) | 0.1 g/L dH2O | 10 mL | 2.05e−09 M |
| Cyanocobalamin | 1 g/L dH2O | 1 mL | 3.69e−10 M |

These micronutrients are stored in two separate solutions ("micronutrients A and B"), Part A comprises F/2 nutrient solution (Table 1) and vitamin solution (Table 3) while Part B comprises trace metal solution (Table 2). Keeping vitamins separate or segregated from trace metal elements allows for storage and prevents the decomposition of vitamins and precipitation of trace metal elements.

Alternative nutrient embodiments may be used to promote the growth of the algae. Such nutrients can be added in solid or liquid forms. The preferred embodiment disclosed before is a two-component micronutrient, but a single-component micronutrient may be used as well. By way of example, nutrients added to the cultivation tank can also include but are not limited to, urea, $NaNO_3$, $MgSO_4$, $NaCl$, $K_2HPO_4$, $KH_2PO_4$, $CaCl_2$, $ZnSO_4$, $MnCl_2$, $MoO_3$, $CuSO_4$, $CoNO_3$, $H_3BO_3$, EDTA, KOH, $FeSO_4$, and $H_2SO_4$. In dark settings, some algal species can switch their metabolism and grow on organic substrates such as glucose, glycerol, and acetate.

Figure 1:
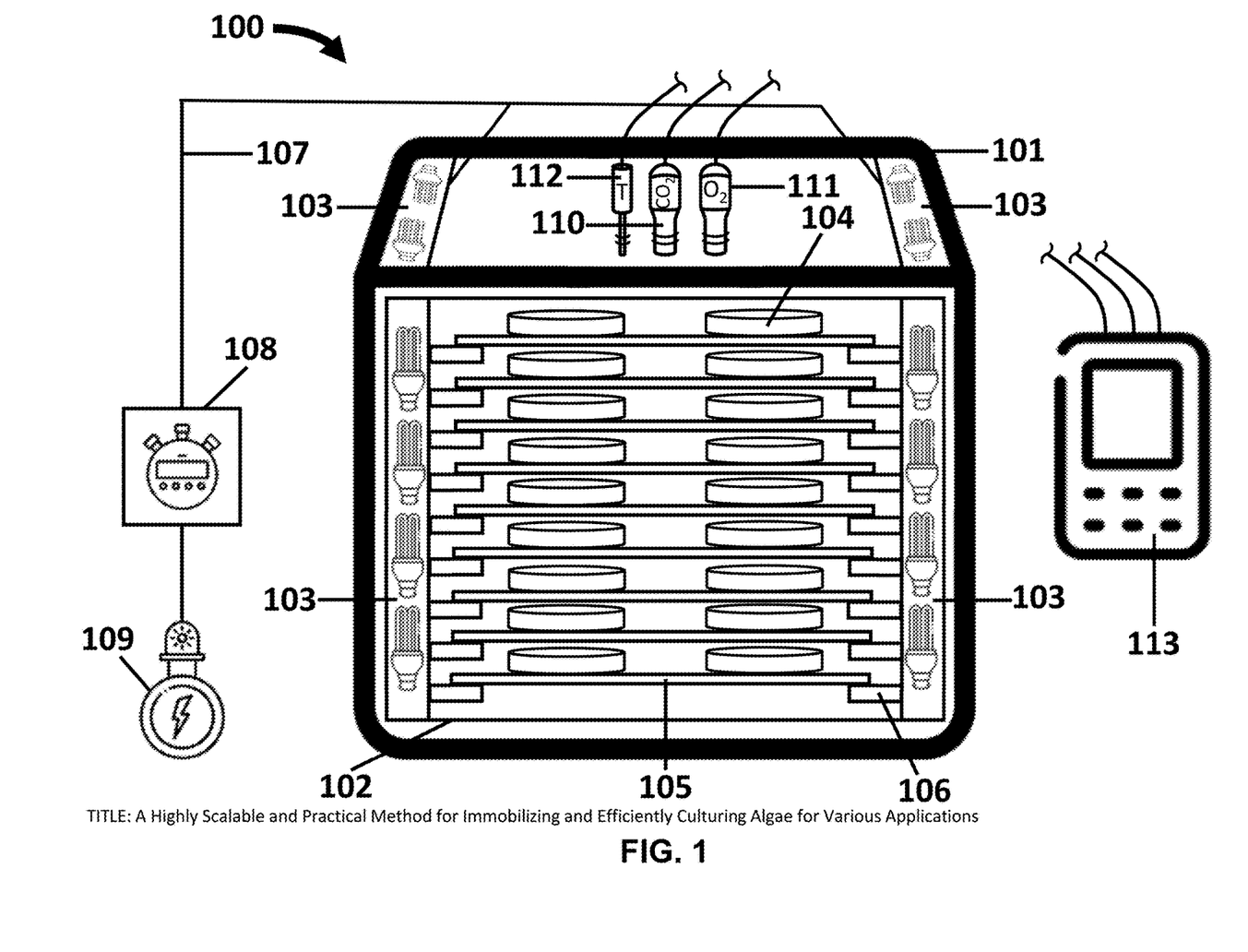
FIG. 1 shows a schematic of the notional photobioreactor (PBR) and monitoring equipment to support algae culturing in a solid medium platform

NOTIONAL PBR, SPECIMEN CONTAINERS, AND MONITORING EQUIPMENT: The method of the present invention to culture algae within a solid medium platform also requires supporting hardware 100 comprising a photon source (e.g., light), a timing means to schedule the lights to turn on or off and monitoring hardware to gauge both environmental conditions and the state of algae growth/population. FIG. 1 shows a schematic of a notional photo-bioreactor (PBR) 101-103, 105-109; a plurality of cultivating containers 104 each holding algae in solid medium ("AiSM") that are open on at least one side to receive light, micronutrients, and exchange gas species; and monitoring equipment 110-113. The following describes the exemplary system to support the second part method of culturing algae in a solid medium. However, it can be appreciated and, for mass production, expected that the PBR, algae container, and monitoring equipment can be of various forms and implementations as long as steps of the later described method for culturing algae are supported and the objectives in the design of the exemplary PBR are fulfilled.

The objectives of an exemplary PBR are to provide the proper sterile environment to support uniform photosynthesis of algae therein, provisions for certain embodiments to periodically add micronutrients to the AiSM, and accommodation of sensing hardware as needed. To that end, the structure of the PBR can be a case 101 with one or more doors 102 or entry points to allow placement within and retrieval of cultivating containers 104 holding AiSM. The volume within case 101 would need to be filled with or allow passage therein of carbon dioxide-containing gas, such as air or exhaust from a power generating plant. The PBR may alternatively have gas injectors (not shown) disposed through said case 101 for the purposes of injecting carbon dioxide-laden gas into said case. Said case 101 can also have an open or openable port to exhaust oxygen and other gases from said PBR.

The exemplary PBR further comprises one or more artificial lights 103 placed strategically within to promote sufficient and uniform lighting of the algae. Alternatively, the light source may be sunlight or an artificial light source outside or external to said case 101 that shines through a substantially transparent case 101 that preferably would be periodically covered to deny the AiSM from receiving light for certain portions of the day or a prescribed period of time so growth processes other than photosynthesis can take place. For external lighting sources, case 101 itself can have an electrochromic film that varies transparency based on whether an electric current is applied to the film or not.

Embodiments of artificial lighting sources may include various types including incandescent lights, fluorescent lights, mercury vapor lights, light emitting diodes (LED), laser, and the like. The light driving the photosynthesis process is known to be achieved using light at a color frequency temperature of up to 7000 K and possibly higher. The example in FIG. 1 depicts internal light panels 103 (white integrated LED edge-lit flat panel flush mount light) attached at the lateral extents within the PBR so that the cultivating container(s) 104 holding the AiSM atop each rack 105 receive sufficient and uniform lighting regardless of placement within the PBR.

Embodiments of said artificial lighting system 103 are electrically connected by some means 107 such as a power cord, in certain embodiments to a timer 108, and then to a power source 109. The purpose of the timer 108 is to allow light to be turned on or off by some schedule over a period of time (e.g., an Earth day).

Sensors such as those for carbon dioxide 110, oxygen 111, and temperature 112 can be disposed through or within the case 101 to monitor the environmental conditions within the PBR and the level of algae culture maturity. Said sensors 110-112 are connected to an electronic device 113 so that signals registered from the sensor may be decoded and displayed in readable format for the PBR's end user. The electronic device 113 may itself or be connected to other devices that log incoming signals into a software application. Collectively, these components 110-113 allow one to non-intrusively infer the state of algae growth and population without having to remove the algae from the PBR.

Alternatively or additionally for other embodiments, a spectrophotometer (not shown) may be used on open or intermittently open(able) systems to more directly quantify the state of algae growth and population. A spectrophotometer can obtain the absorbance values for pigments found most abundantly in *Chlorella vulgaris* ("Cv") and the acquired data is traced and graphed over time. Absorbance values at the wavelengths 430.4 nm and 662.0 nm (corresponding to chlorophyll a) and 449.9 nm and 639.8 nm (corresponding to chlorophyll b) are recorded. The preference is to set the parameters in terms of chlorophyll a, as it is the primary pigment of photosynthesis while b is an accessory pigment.

Each rack 105 in the example is made of sterilized sheeting and placed atop a pair of sterilized rack rails 106 affixed and protruding inward from the opposing lateral panels of the PBR case 101. Alternative PBR embodiments may forgo the use of racks 105 and rack rails 106 and instead use a means to hang (not shown) the cultivating containers 104.

The PBR may be an open, intermittently open(able), or closed system. In an open system, the photosynthetic gas exchange process occurs continuously and passively through unsealed boundaries of the PBR system. In addition, micronutrients supportive of algae growth may be added. In a closed system, the PBR is fully sealed and no gas exchange occurs across the PBR system boundaries nor can micronutrients be added during the culturing process. For an intermittently open system, the PBR generally acts like a closed system during algae cultivation, except certain elements are individually added (carbon-dioxide-laden gas, micronutrients) or scavenged (oxygen-rich gas) by active means.

For example, in an intermittently open(able) system, micronutrients may be added via open valve (not shown) connected to a discharge tube or nozzle that leads to each of the cultivating containers 104, and after adding the micronutrients, the valve is closed. With other intermittently open(able) system embodiments, carbon dioxide-containing gas may also be added inside the PBR. Because the administration of light beyond a certain threshold may compromise the productivity of algal cultures, in the absence of sufficient carbon dioxide, an intermittently open(able) system in conjunction with a carbon dioxide sensor 111 and a logic circuit referencing the time the light was on may be used to quantify and properly meter the quantity of carbon dioxide to optimize algal culture productivity during the lighted portions of a light cycle.

CREATION AND MAINTENANCE OF AN ALGAE CULTURE SUPPLY: In addition to a PBR and micronutrients, another foundational aspect that needs to be established before the disclosed methods are carried out is the creation and maintenance of an algae culture supply ("ACS"). The following procedure, based on a reference by Allaguvatova et al. [10] was written to create 12 L of Cv algae species but may be applied to numerous other algae species. This method is easily extended to different quantities by applying equivalent ratios of constituent ingredients. For identification purposes, the step number is prefixed with "ACS."

Step ACS1: Obtaining a solution of 500 mL Cv.

Step ACS2: Creating a 500 mL micronutrient solution by adding filtered or distilled water to a sterilized 2000 mL jar, adding 0.5 mL each of Guillard's F/2 micronutrients A and B, then stirring with a glass rod to incorporate.

Step ACS3: Pouring the algae culture into the sterilized jar to create an algae culture solution (ACS).

Step ACS4: Screwing or more generally attaching a lid onto the top of the jar, wherein said lid is provisioned to receive airflow and circulate the algae so that all algae over time is exposed to carbon dioxide and provisioned light source. For certain embodiments, the lid can have a circular cutout with one end of a rubber tube disposed through the lid and into the ACS solution with the other end attached to the outlet of an air pump. A flexible hollow plastic rod may first be passed through a portion of said rubber tube to add some rigidity and facilitate the passing of the tube through said lid. The remaining lid cutout area may be plugged or sealed, such as with a circular sponge.

Step ACS5: Placing the algae solution on a shelf several inches from an artificial light supply, up to 7000 K color frequency temperature, but preferably near 6000 K. This light should be attached to a timer 108 so that a consistent cyclical schedule of light followed by darkness can be executed. A natural light source (i.e., sunlight) may be alternatively used.

Step ACS6: Adjusting the air pump so that the solution circulates and allows all algae within the solution to periodically access light and carbon dioxide. The supplied air acts as a jet to agitate and generate/maintain angular momentum (i.e., stir) to the bulk mixture. The preferred angular speed or frequency of the bulk solution in the jar is approximately 100 rpm. The solution is preferably maintained at approximately 25° C. [10] to stimulate the optimal culture yield within a given period.

Step ACS7: Allowing the culture to grow.

Step ACS8: Every three days, performing a "water change" process comprising the splitting of each culture into two new jars, with care being added so as not to include the dark detritus at the bottom of the jar. Then adding micronutrients at a concentration of 0.5 mL each of parts A and B per 1000 mL algae solution. Finally, adding 500 mL water to each jar to replenish the lost volume. Allowing the culture to grow. Then repeating this process over the course of approximately a month or when the desired algae supply (e.g., 12 L algae) is generated. This solution will continue to be referred to as the algae culture solution "ACS" in Step 201a in the following section describing the METHOD OF PREPARING A SOLID MEDIUM ALGAE SPECIMEN.

METHOD OF PREPARING A SOLID MEDIUM ALGAE SPECIMEN: The following outlines the first of two methods of the present invention, that is to prepare a solid medium algae specimen 200 which is described below and outlined in FIG. 2.

Figure 2:
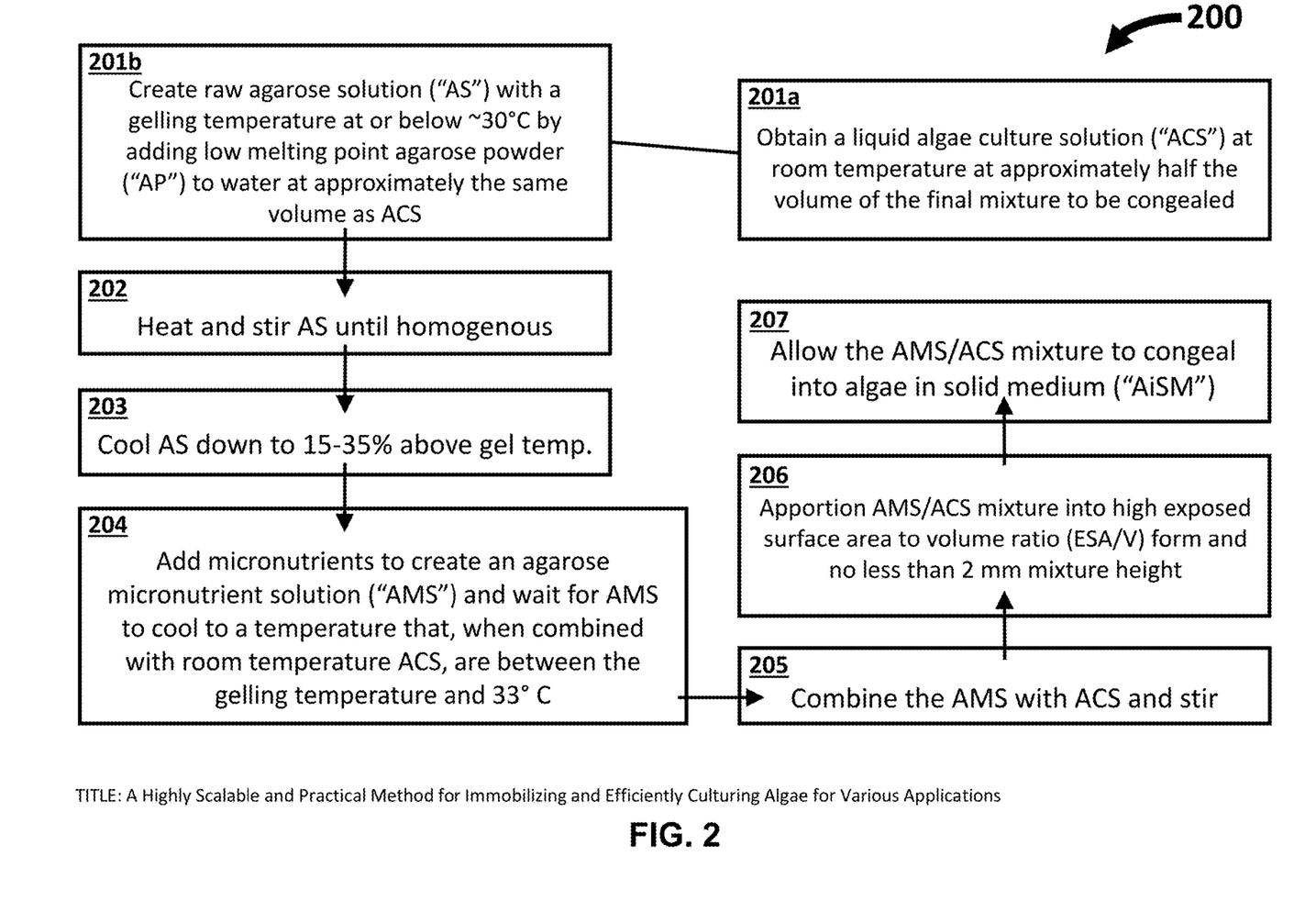
FIG. 2 is a block diagram showing the steps to preparing an algae in solid medium (AiSM) specimen

Step 201a: Once the stock of Cv algae culture solution ("ACS") is created or acquired (see previous section on the CREATION AND MAINTENANCE OF AN ALGAE CULTURE SUPPLY), obtaining a specific amount for the current specimen in a liquid container at room temperature or around 20° C. The amount should be approximately the same as the agarose solution ("AS") that will be obtained in the following step or approximately half the volume of the final mixture to be congealed in Step 207. This collection should preferably occur on the day following the water change process discussed in Step ACS8 of the previous section.

Step 201b: Creating raw agarose solution ("AS") by adding low melting point agarose powder ("AP") to filtered or distilled water of similar volume as the ACS in a sterilized container (e.g., beaker) that is different from the one used for the ACS. This mixing ratio is based on the use of an AP with properties listed in Table 4, said properties corresponding to Benchmark Scientific® Agarose LM [11]. For the exemplary embodiment, a 2% AS was created with this particular AP at a ratio of 1 gram AP per 50 mL water.

TABLE 4

Properties of Benchmark Scientific® Agarose LM [11]

| Property | Value |
| --- | --- |
| Moisture | <=10% |
| EEO (electroendosmosis) | <=0.1% |
| Sulfate | <=0.1% |
| Gelling Temp. @ 1.5% | 26-30 deg. C. |
| Melting Temp. @ 1.5% | <=65 deg. C. |
| Gel Strength | >=200 g/cm^2 (1%) |
| Resolution | 200 bp to 25 kbp |

Step 202: Heating and stirring AS until the mixture is homogeneous. The heating means may be by convection or radiation (microwave) mechanism. The heating may be periodically suspended so that the mixture may be stirred to accelerate the homogenization process of the mixture before reheating. This process is repeated until there is no visible trace of the agarose powder in the AS.

Step 203: Cooling or waiting for the AS to cool down to preferably approximately 25% above the gelling temperature of the AS. For the exemplary AP used to create the AS, 25% above the 30° C. upper end-of-the-range gelling temperature is 37.5° C. The preferred 25% buffer above the gelling temperature range listed in Table 4 allows the following Steps 204-206 to be carried out without concern about premature gelling of the final mixture. This value may be adjusted based on ease in advancing through the steps and the specific properties of the exemplary AP and AS; hence the viable range may reasonably span between approximately 15% to 35% above the gelling temperature of the AS.

Step 204: Once the AS cools to a temperature between approximately 15-35% above the gelling temperature of the AS, adding a micronutrient supportive of algae growth. For embodiments with properties equivalent or similar to Guillard's F/2 micronutrients with parts A and B, adding each part at approximately a ratio of 1 mL for every 2000 mL to the AS to create an agarose micronutrient solution ("AMS"). For example, if there is 250 mL of AS, then 0.125 mL of micronutrient part A and 0.125 mL of micronutrient part B are added to the AS. Following this, the AMS is allowed to cool.

Step 205: Once the AMS has cooled to a temperature where the simple average of the AMS temperature and room temperature (~20° C.) ACS is above the gelling temperature of the AMS at the lower end and 33° C., then combining the AMS with approximately room temperature (~20° C.) ACS by mixing the two (AMS and ACS) into a sufficiently large open container and stirring.

In the later described example in the EXAMPLE section, a 33° C. AMS temperature threshold was chosen to begin mixing the AMS and ACS to homogeneity as it is high enough to obviate concerns about premature gelling yet is low enough that the live algae culture in the ACS would not be exterminated from excessively high temperatures when the AMS and ACS are mixed together. Mixing equal volumes of AMS and ACS should indicate an eventual upper-bound bulk mixture temperature of 26.5° C. based on the simple average of room-temperature ACS of 20° C. and the preferred and proposed 33° C. threshold of the AMS for the ACS and AMS to be mixed together. 26.5° C. is just above the 26° C. lower-end range of the gelling temperature for the exemplary AP used to create the AS. As summarized by the reference of Serra-Maia et al. [14], "Microalgae are typically able to develop over a wide range of temperatures between 15 and 35° C. [15] . . . Cell mortality takes place at temperatures in a range (depending on the species) between 20° C. and 45° C. [16]." The third figure in Serra-Maia [14] shows the Cv mortality rate sharply increasing above approximately 26-27° C. Hence, 33° C. is a suitable AMS temperature to begin Step 205, since this temperature collectively accounts for this mortality rate by temperature, the gelling temperature of the exemplary AMS, and practical mixing time. Prudently, in view of these, the average bulk temperature of the ACS and AMS at the time of mixing together should be in the range of the gelling temperature of the AMS in the lower end and 33° C. with the preferred upped range temperature being below 28° C.

Step 206: Apportioning AMS/ACS mixture into a low aspect ratio cultivating container 104 to produce a high exposed surface area to volume ratio form.

At the bulk scale, this is generally set by the geometry of the cultivating container 104 the AMS/ACS mixture is poured. Preferably, the agar plate or cultivating container 104 would have a low aspect ratio (AR, height to some base dimension) profile. Past experimentation with square base cultivating containers 104 of 245 mm edge length with a height of 25 mm showed excellent algal productivity. The AR=height/edge length would be approximately 0.10. If this cultivating container 104 was filled with the AMS/ACS solution to the brim, the exposed surface area (top surface only) relative to the volume would equate to an ESA/V ratio of approximately 153.

In terms of other base surface geometries, if the base is a straight-edged (faceted) shape with non-equilateral edges, a general formula for AR would be the height of the container 104 divided by the average length of each edge in the base. If the base is a circle, the AR would be the height of the container 104 divided by the diameter of the base circle. If the base is an ellipse, the AR would be the height of the container 104 divided by the average of the major and minor axis dimensions. Hence, based on past experimentation an AR approximately equal to or less than or approximately 0.1 is recommended and the cross-sectional form along the height of the container 104 is assumed to be constant.

Experimentation has shown algae can be cultured in solid medium productively with an ESA/V over 100. Lower ESA/V ratio values, such as 10, while viable for algae growth, have less surface area for gas exchange and potentially reduce productivity rates with all other factors being the same. Conversely, higher values enhance productivity rate.

For a given volume of liquid mixture, a higher ESA/V ratio corresponds with a lower mixture height and a relatively wider footprint. This wider footprint translates to greater infrastructure demands to maintain uniform light exposure to all algae specimens. Furthermore, the drive to increase the ESA/V ratio and reduce the mixture height is tempered by a faster agar dry-out rate. Approximately 2 mm has been found to be the minimum prudent AMS/ACS mixture height to avoid premature agar dry-out. The proper minimum height can vary based on conditions in the PBR (e.g., temperature, humidity, light intensity, the velocity of the gas in the PBR, etc.). Therefore, it is advised to pour the AMS/ACS mixture across the widest possible area defined by the geometry of the cultivating container 104 under uniform lighting at a height of no less than 2 mm. This 2 mm would be an overriding limiting criterion.

Alternatively, instead of having the threshold for avoiding premature dry-out be an overriding lower bound, it may be one of the governing parameters with the other being the ESA/V ratio of over 100. Reduced to guidelines, this can be reasonably stated as the AMS/ACS mixture for each container 104 whose base geometry is defined by a 2-10 mm apportioned mixture height and a base geometry set to provide a mixture ESA/V ratio higher than 100. This range considers the aforementioned 2 mm limiting criterion and the 8.33 mm height successfully used in experimentation. Modifications to the exposed surface topology to add surface roughness and increase the total area may also be carried out to enhance the algae productivity or yield rate via augmented ESA/V.

Step 207: Waiting for the mixture to congeal into algae in solid medium ("AiSM").

METHOD OF CULTURING ALGAE WITHIN A SOLID MEDIUM: The following outlines steps of the second of two methods of the present invention, which is to cultivate AiSM 300. The steps are listed below and shown in FIG. 3.

Figure 3:
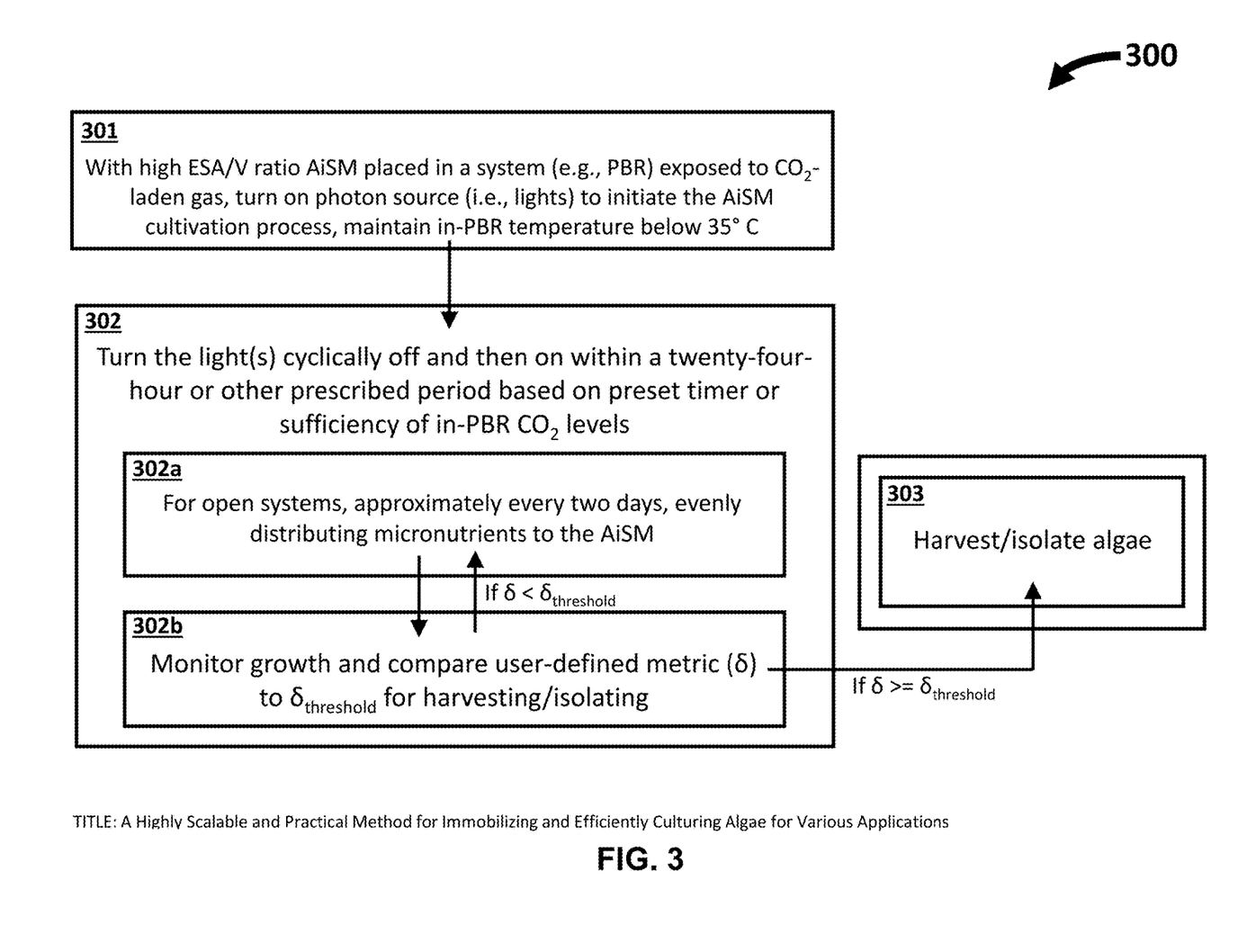

Step 301: With the high ESA/V AiSM placed in a system (e.g., PBR) exposed to $CO_2$-laden gas, turning on a photon (e.g., light) source to initiate the actively controlled AiSM cultivation process. The AiSM may be apportioned across one or more cultivating containers (e.g., sterilized petri dish) 104. The AiSM may also be outside the PBR as long as it is placed where it can receive light and has some initial carbon dioxide to ingest. Ideally, the temperature of the AiSM and gas the AiSM is exposed to is under 35° C., preferably under 30° C., and to be optimal, as close to 25° C. as possible [12].

Step 302: Turning the light(s) cyclically off and then on within a twenty-four-hour or other prescribed period during algae growth, during which Steps 302a and 302b are executed. The on-off light cycling can follow a twelve-hour light and twelve-hour dark (12:12) pattern.

References report varying ranges and optimal ratios of light and dark time durations for a given cycle [10]. Ultimately, in practice, the proper on-off cycling schedule may be dependent on the surrounding carbon dioxide concentration and other factors, which in turn may vary. Variations of the 12-hour:12-hour pattern using a different on-off time ratio can be used and may be actively adjusted and the cycle need not necessarily be one day long. For example, insufficient carbon dioxide may be used as a trigger to alter the schedule and turn off the lights. During the "rest" period when the lights are off, the theory states that algae's cellular respiration shifts to ingesting oxygen rather than carbon dioxide. Alternatively, for this carbon dioxide-deficient scenario, instead of varying the on-off scheduling, additional carbon dioxide may be pumped into the PBR. Conversely, if there is excess or sufficient carbon dioxide, the on-light schedule may be extended and/or carbon dioxide-laden inlet gas flowrate may be throttled down or isolated by use of a valve, case shutters, sealed case door(s), and the like.

Step 302a: For open systems or intermittently open(able) systems, approximately every two days, adding and evenly distributing micronutrients to the AiSM. Embodiments of the method may have the micronutrients in liquid solution form ("MS").

If the micronutrients are equivalent to the two-component Guillard's F/2 micronutrient mentioned earlier, a volume ratio of approximately 25:1 between the volume of the earlier produced AMS/ACS mixture before it congealed into AiSM and the currently to-be-added MS in liquid form is suggested. The MS itself is made from a ratio of distilled or filtered water to each micronutrient part at a ratio of approximately 77:1.

For example, if 500 mL of combined AMS and ACS was prepared in Step 205, then the nourishment step here would be to take 20 mL of filtered or distilled water, add 0.26 mL of micronutrient part A, and 0.26 mL of micronutrient part B, mix them as the new MS and then pour the MS evenly across the AiSM surface. Other ratios may be used based on the properties of the micronutrient used.

The even liquid MS distribution can be further assured by gently tilting and rotating each of the cultivating containers 104 several degrees. Alternatively, the solution may be sprayed with a fine mist all around the AiSM surface by manual and/or mechanized means.

Step 302b: Monitoring growth and comparing against a user-defined metric ($\delta$) for harvesting/isolating. If $\delta < \delta_{threshold}$, then repeating Step 302a. If $\delta < \delta_{threshold}$, proceed to Step 303.

The $\delta$ metric can be based on the number of properties that are conveniently available to the one applying this method, available configuration and environment of the PBR, monitoring equipment, and production end goal. For example, if the production goal is lipid production for biofuels, the $\delta$ metric can be lipid productivity measured in mass/volume/time period (e.g., mg/L/day). Daliry et al. [13] reported an optimal of 66.25 mg/L/day for their investigations. For a given production facility's attainable, optimal/peak yield rate, a $\delta_{threshold}$ may be set based on economic and Pareto optimal considerations that may be somewhat below the peak if the yield rate follows a substantial rise and fall temporal trend. This can equally apply to the other metrics described below.

Alternatively, if edible vulgaris biomass is sought, another metric may be used, such as the instantaneous or short period (e.g., daily) biomass production rate expressed in mass/volume (e.g., gm/L) terms. What may be a $\delta_{threshold}$ for one condition may be too high for another condition if available lighting power, light targeting, carbon dioxide, etc. are constrained (e.g., PBR during winter in far north latitude using natural sunlight as the sole light source).

Another candidate metric is the optical density, which additionally requires a properly aimed camera(s) and an image processing application for quantifying the optical density [10]. The public domain software, ImageJ, as well as the image processing toolkit from MATLAB® may be used. In this method, photographs of algae plates are taken under the same lighting conditions and camera settings, and density is analyzed using an ImageJ application.

The growth rate of algae quantified using a microscope viewing one of the AiSM samples and visualization software to tally the number of cells within an observation volume is another potential metric [10]. The growth rate may be defined as the $\ln(N_2/N_1)/(t_2-t_1)$, where $N_2$ and $N_1$ are the numbers of cells at times $t_2$ and $t_1$, respectively.

As mentioned in the section NOTIONAL PBR, SPECIMEN CONTAINERS, AND MONITORING EQUIPMENT, another approach to quantifying the algae population density and rates of change for open or intermittently open(able) systems is spectrophotometry. Here, the solid medium algae can be cut from the dish to place within a cuvette for analysis. Alternatively, for closed systems, carbon dioxide 110 and oxygen 111 sensors may be used to infer the state of algae population density and rates of change.

Step 303: Harvesting/isolating the matured algae.

Example

The following is an account of an actual experimental campaign that was carried out with results that validate the viability of the disclosed methods. This was accomplished by observing and quantifying the growth of Cv in different structural compositions (liquid versus solid medium) within a photobioreactor system.

PREPARATION: The PBR is schematically approximated by FIG. 1, case 101, door 102, rack 105, and rack rails 106 are made from substantially transparent acrylic. The rack 105 and rack rails 106 were further sterilized before use. The AiSM is contained in standard height, non-treated, and sterilized Nunc™ Square BioAssay (Petri) Dishes 104.

The lighting panel 103 is a Commercial Electric® 1 ft.×1 ft. 10-Watt Dimmable White Integrated LED Edge-Lit Flat Panel Flush Mount Light with Color Changing CCT. The color frequency is adjustable between 3000 K, 4000 K, and 5000 K, where 4000 K was used for this example. A timer 108 was attached to the light panels' power cord 107 that was plugged into a power source 109 to govern the light's on-off triggering based on a schedule and was set to twelve hours of light followed by twelve hours of darkness. The light panels were placed at the PBR's sides (approximately 2.5 inches) from the algae itself. Both the light color frequency and distance of the light from the culture can be changed and lead to the same result of algal growth.

Two different PBRs were used in the experiment. One was a closed/sealed system, where duct sealant was placed around the door's perimeter 102 to prevent air escape. Hence the captured carbon dioxide before PBR sealing was the only supply throughout the duration of the experiment. Carbon dioxide 110, oxygen 111, and temperature 112 sensors along with a Vernier LabQuest® Mini sensor interface were used to quantify the state of algae growth. The second PBR system was an open system where a continuous gas exchange was possible, micronutrients were periodically added, and a Vernier Go Direct® SpectroVis Plus Spectrophotometer was used to quantify the state of algae growth. The reason for the open PBR experiment was to provide another means of quantifying algae growth and to gauge whether further periodic addition of micronutrients (even though an initial amount is already in the agar plates) can result in a further increase in algae population density.

As mentioned, to gauge the viability of the disclosed methods for AiSM, a companion experiment using liquid medium algae in closed and open PBRs was run, and applied the best practices for liquid medium Cv growth [10]. The state of AiSM growth using the methods described was benchmarked against the liquid medium algae growth measurements and the results are presented below in the RESULTS AND DISCUSSION section. The duration of the experiment was two weeks.

PREPARING THE AiSM: Steps 201a-207 in the section describing the METHOD OF PREPARING A SOLID MEDIUM ALGAE SPECIMEN were followed. Specifically in Step 201a, 250 mL of ACS was obtained. In Step 201b, 5 grams of low melting point AP (Benchmark Scientific® Agarose LM [10]) was added to 250 mL filtered water in a 500 mL beaker to create 250 mL AS.

In Step 202, the AS was heated in a 600-watt microwave oven in 30-second intervals. Every 30 seconds, the mixture was removed from the microwave, stirred vigorously with a glass stirring rod, then placed into the microwave once again. This process was repeated until no trace of the white agarose powder was seen.

In Step 204, once the AS reached a temperature of approximately 37.0° C. for the exemplary AP used to create the AS, a micronutrient supportive of algae growth was added. In the case of Guillard's F/2 micronutrient [9], 0.125 mL each of micronutrients A and B were added to create AMS.

In Step 205, once the AMS reached a temperature of approximately 33.0° C., the 250 mL ACS obtained in Step 201a was mixed together with the AMS. The AMS/ACS mixture was stirred rapidly with a glass stirring rod, then poured into a 600 mL petri dish where it was allowed to solidify. Alternative embodiments may be to apportion the mixture into cultivating containers 104 like a 245 mm diameter×8.33 mm high circular base container 104 or 245 mm square base×25 mm high one. It is advised to pour the AMS/ACS mixture across the widest possible area where uniform lighting can be delivered onto a high ESA/V (and hence potentially high yield rate) specimen, but the AMS/ACS mixture should not be less than 2 mm due to concerns below that threshold related to premature drying.

CULTURING: Next, Steps 301-303 in the section describing the METHOD OF CULTURING ALGAE WITHIN A SOLID MEDIUM were followed. Specifically, the timer 108 was set to a twelve-hour light followed by a twelve-hour dark cycle. Every 2 days, 20 mL micronutrient solution (20 mL filtered water with 0.26 mL of each micronutrients A and B) is added on top of the solid medium culture. The solution itself was evenly distributed over the solid medium surface to ensure even micronutrient distribution which was accomplished by gently tipping the dish back and forth.

QUANTIFICATION METHOD: Spectrophotometry was used to measure absorbance values to determine pigment increase of the culture over time in the open PBR. Before spectrophotmetry measurements, a sample of each culture is taken; this is achieved by using a pipette and mixing the liquid in the liquid medium petri dish before placing a sample within a cuvette, and homogenizing a portion of the solid medium algae that is cut from the dish to place within a second cuvette.

The wavelengths 430.4, 662.0, 449.9, and 639.8 nm correspond to pigments chlorophyll a, chlorophyll a, chlorophyll b, and chlorophyll b, respectively. These pigments are found in the highest abundance within Cv. The values of each of the chosen absorbance wavelengths are first averaged, then entered into a table showing the mean absorbance for each wavelength on each day. The RESULTS AND DISCUSSION section will mostly present results posed as percent change in population density that correspond to percent change in pigment absorbance values for chlorophyll a, or 430.4 and 662.0 nm, because as mentioned, chlorophyll a is the primary pigment of photosynthesis while chlorophyll b is an accessory pigment.

For the closed PBR, due to the lack of noticeable change in oxygen gas concentration during the experimental period (maximum of −0.015% change per day), data on carbon dioxide consumption was determined to be the most reliable for growth tracking. Oxygen gas may be trapped within the solid medium algae in the form of bubbles observed during the experiment, thus diminishing the reliability of the oxygen production display. As such, the change in carbon dioxide concentration was utilized to represent the photosynthetic productivity of each system, while temperature was used to determine controlled experimental conditions.

Errors have been limited through a multitude of precautionary measures. This includes sterilizing all materials before and after use, using a mask while in the laboratory to prevent contamination, disposing of any contaminated materials, and timing all measurements precisely, among other practices. For data collection, a total of 14,814 data points (each with a temperature, oxygen, and carbon dioxide value) are collected and analyzed to ensure experimental consistency; the same goal is met in spectrophotometry by collecting absorbance data three separate times and finding the means of such values to draw conclusions from. The largest known error in experimentation was an electrical failure, wherein five hours of gas and temperature data were lost due to a power outage. This error was compensated for by using the mean method to track growth. While it affected an isolated portion of the data, the remaining data was unaffected, as the mean calculation resets every twelve hours.

Figure 4:
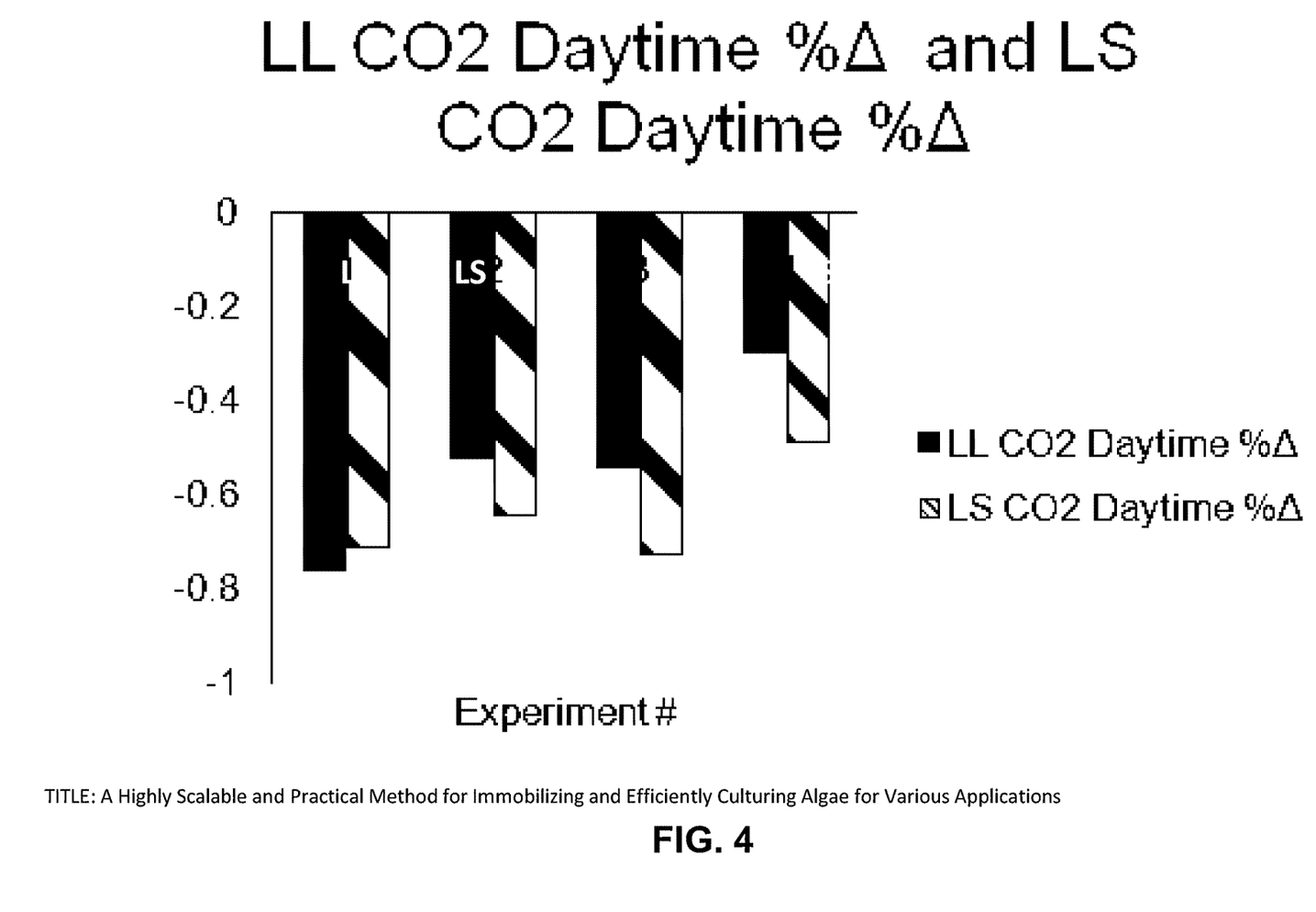
Figure 5:
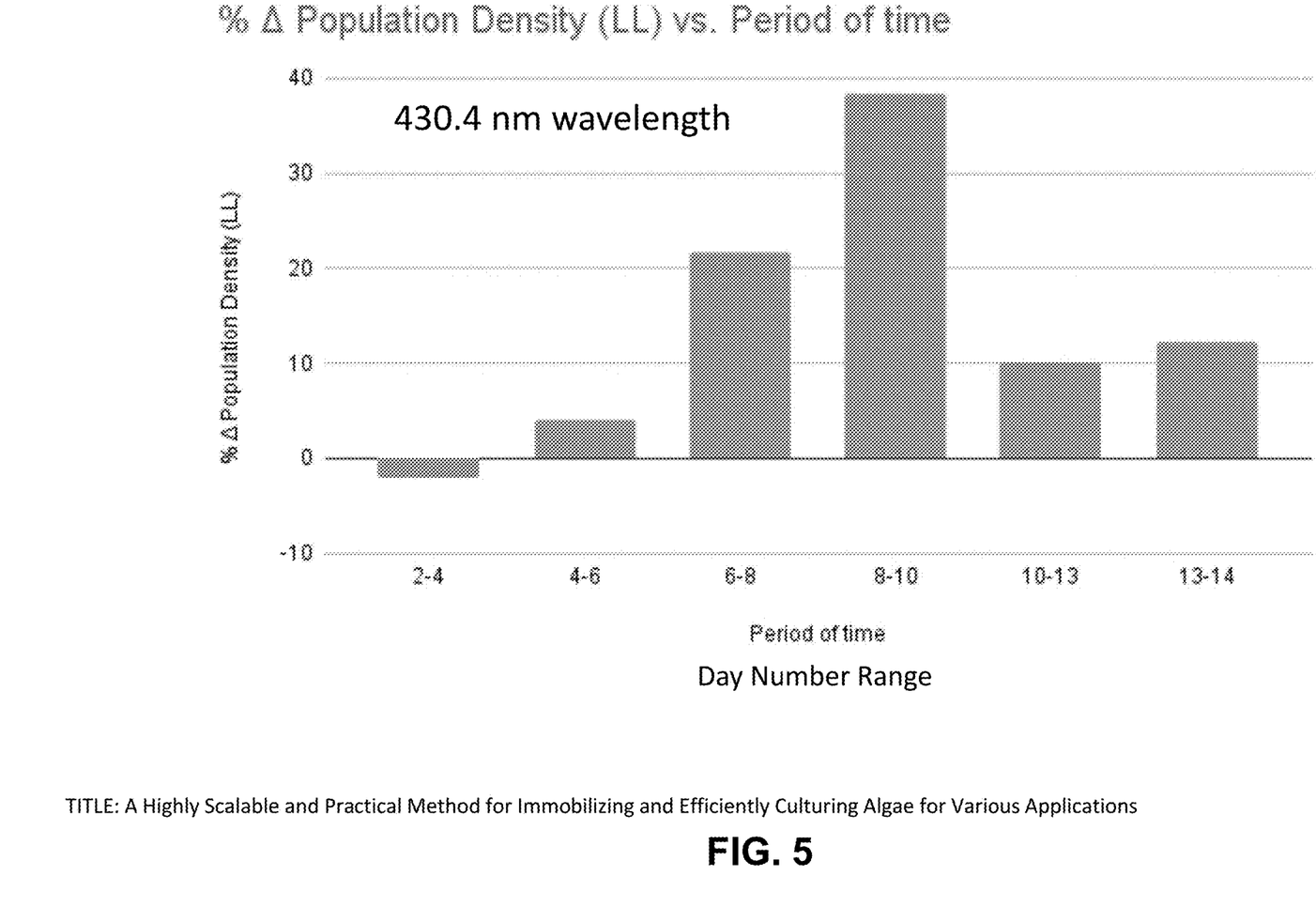
Figure 6:
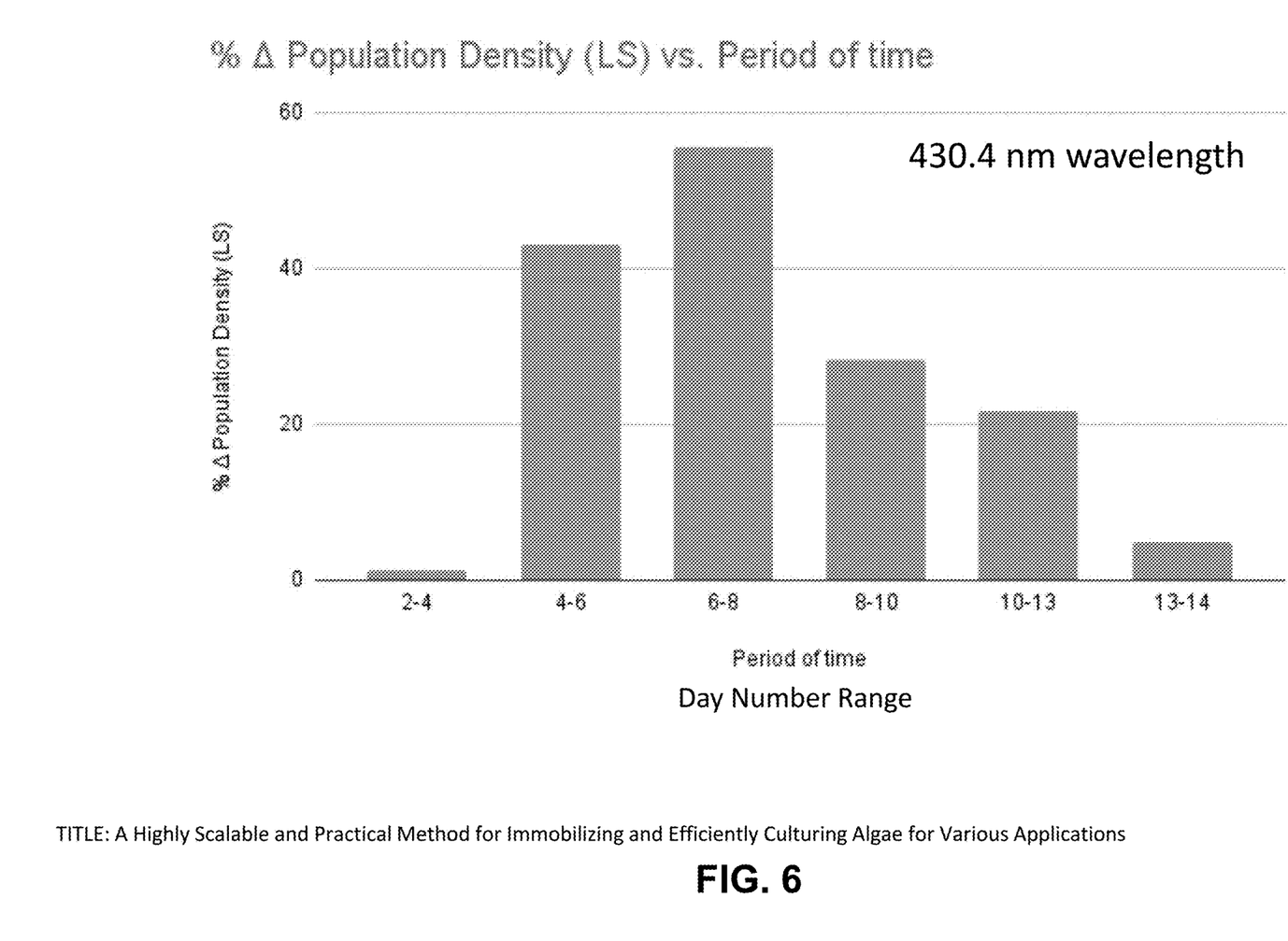
Figure 7:
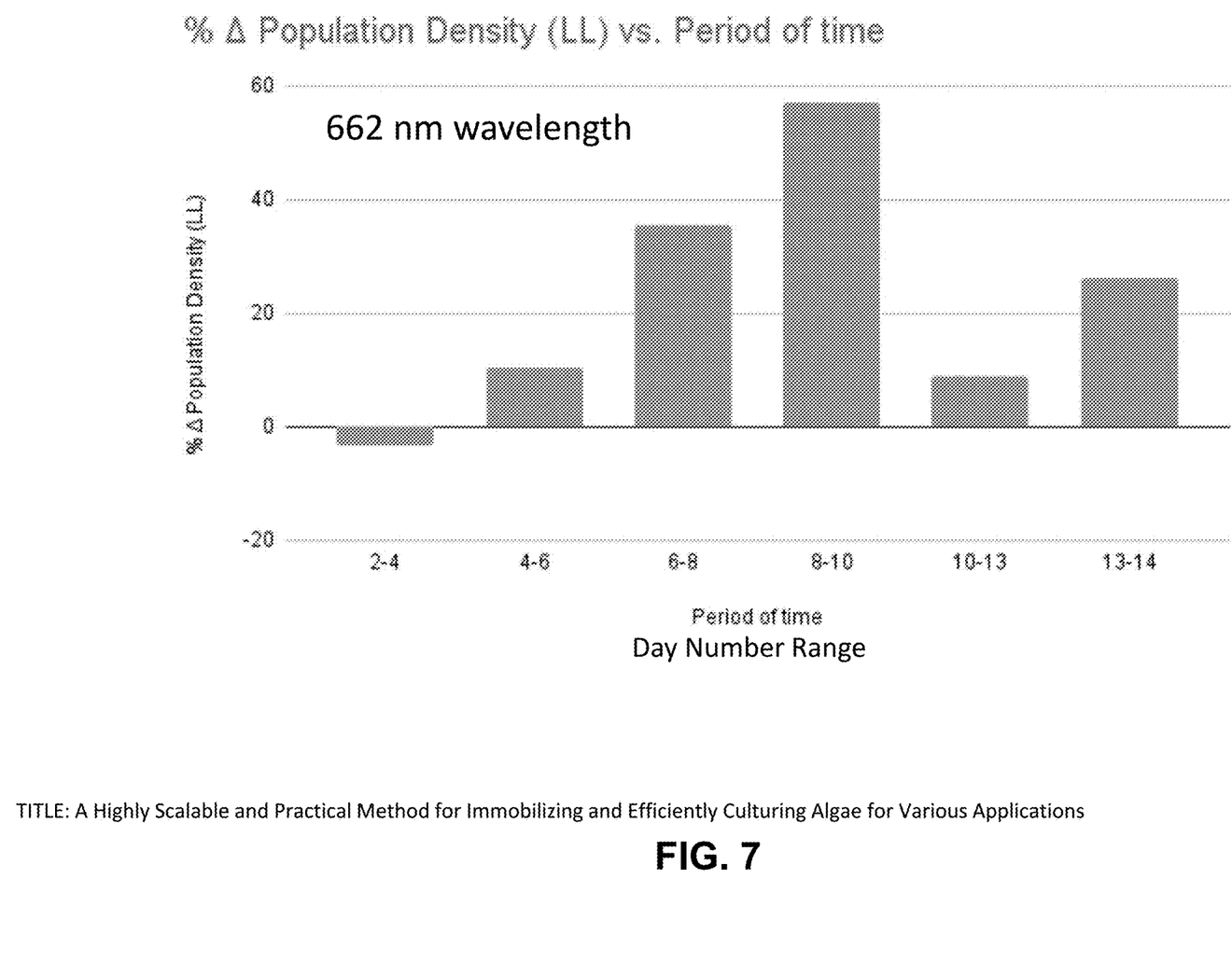
Figure 8:
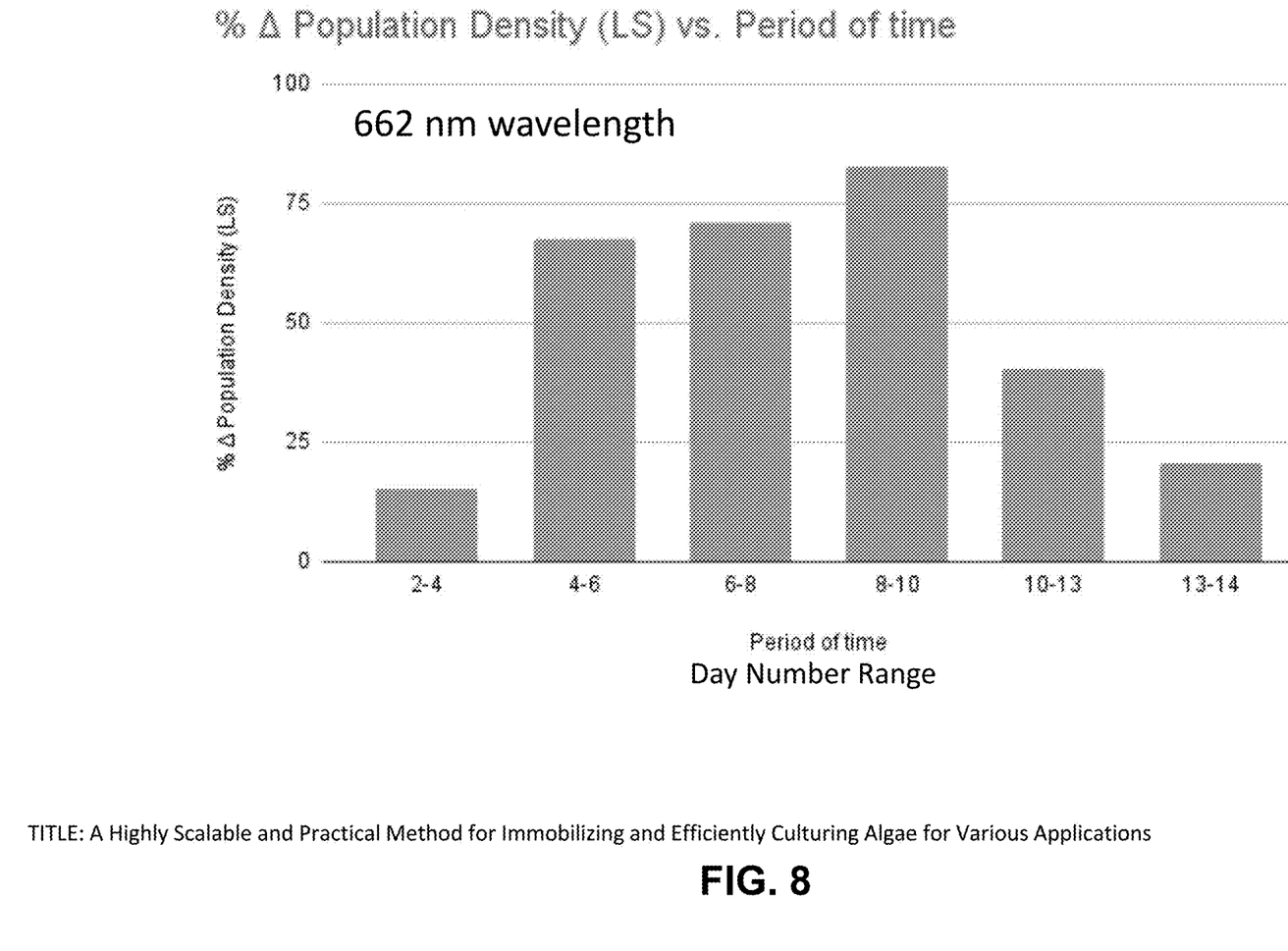

RESULTS AND DISCUSSION: As observed in FIG. 4, both solid and liquid media systems show noticeable carbon dioxide consumption with growth sustained during both weeks of growth for both systems, proving the potential for long-term cultivation. Over the 14-day period with no added micronutrients, each system decreased its cores' carbon dioxide concentration by more than 0.5% per 12-hour light cycle. More specifically, the solid media system outperforms its liquid counterpart over time, with −0.6416% and −0.5305% (solid and liquid media, respectively) showing the solid media's consumption efficiency to be 20.96% higher. Mean fluctuations in temperature (not shown) did not differ by more than 1%, providing support that experimental conditions are well controlled between both cores.

Analysis of spectrophotometry data of the open PBR cultivated samples corroborates the findings, as shown in FIGS. 5-8. In spectrophotometry analysis, algae in solid media show up to an average 47.49% growth rate (662.0 nm), compared to the 21.98% growth rate of algae in liquid media (662.0 nm). Also during the experimental period, the solid media culture displayed growth from 11.68% (@ 430.4 nm) to 28.27% higher (@ 639.8 nm, not shown) than liquid. Another pattern noted over the period is the earlier percent rise in solid media growth, with the percent change in absorbance between days 2-8 being up to 60.58% higher in solid media compared to liquid (Experiment 4, 662.0 nm). During days 8-14, the percent change in absorbance (at wavelengths 430.4 nm and 449.9 nm that is not shown) of the solid media algae decreases to the same value as liquid media, while absorbance at wavelengths 639.8 nm (not shown) and 662.0 nm remains higher than the liquid media. Of note, the most significant decrease in percent change is noted between days 13-14, when the absorbance value for solid media algae reaches the maximum measurable absorbance value of 3.000.

With regards to the user-defined metric ($\delta$) discussed earlier in Step 302b, if the metric ($\delta$) is the population density change, then the $\delta_{threshold}$ can be defined as some cutoff value (e.g., 25%), below which harvesting/isolation (Step 303) can then carried out. Alternatively, high-yield applications may require a peak detection approach, that for trends that are roughly bell-shaped, is straightforward to detect and a cutoff threshold ($\delta_{threshold}$) can be derived that maximizes the average production rate.

In earlier experimentation conducted by the primary investigator of this experiment, spectrophotometry was utilized to determine the growth of algae in various media. This was performed on a small scale, using 10 mL petri dishes, in contrast with the 500 mL petri dishes used in the current experiment. The previous experiment's results showed similar results, with algae in a solid medium showing favorable and sustainable growth. The fact that the growth cycles of both systems are replicable is a testament to the potential scalability of such a system.

Many alterations and modifications may be made by those having ordinary skill in the art without departing from the spirit and scope of the embodiment. Therefore, it must be understood that the illustrated embodiment has been set forth only for the purposes of example and that it should not be taken as limiting the embodiment as defined by the following claims. For example, notwithstanding the fact that the elements of a claim are set forth below in a certain combination, it must be expressly understood that the embodiment includes other combinations of fewer, more, or different elements, which are disclosed herein even when not initially claimed in such combinations.

Benchmark Scientific® is a registered trademark of Benchmark Scientific Inc.

Algae Research and Supply® is a registered trademark of Matthew P Huber.

Nunc™ is a registered trademark of Nunc A/S.

Commercial Electric® is a registered trademark of Home Depot Product Authority, LLC.

MATLAB® is a registered trademark of The MathWorks Inc.

LabQuest® is a registered trademark of Vernier Software & Technology LLC.

Vernier Go Direct® is a registered trademark of Vernier Software & Technology LLC.

REFERENCES

1. Luangpipat, T. and Christi, Y. "Biomass and oil production by *Chlorella vulgaris* and four other microalgae—Effects of salinity and other factors." Journal of Biotechnology, Vol. 257 (Sep. 10, 2017): pp. 47-57.
2. Mathewson, S. "Algae 'Bioreactor' on Space Station Could Make Oxygen, Food for Astronauts." May 8, 2019. Retrieved Apr. 5, 2023. https://www.space.com/space-station-algae-experiment-fresh-air.html.
3. Masojídek, J. and Torzillo, G. "Mass cultivation of freshwater microalgae. Encyclopedia of Ecology." Encyclopedia of Ecology, Aug. 6, 2008, pp. 2226-2235. Retrieved Jan. 16, 2023. https://www.sciencedirect.com/science/article/pii/B9780080454054008302.
4. Detrell, G., et al. "PBR@LSR: The Algae-Based Photobioreactor Experiment at the ISS—Configuration and Operations." 49th International Conference on Environmental Systems, Boston, Mass., USA. July 2019.
5. Detrell, G., et al. "PBR@LSR: the Algae-based Photobioreactor Experiment at the ISS—Operations and Results" International Conference on Environmental Systems, July 2020.
6. Belcher, H. and Swale, E. "Culturing Algae: A guide for schools and colleges." Cambridge, U.K. Institute of Terrestial Ecology. p. 22. Retrieved Mar. 10, 2023. https://nora.nerc.ac.uk/id/eprint/5236/1/Culturing_algae.pdf.
7. Shirai, M., et al. "Development of a Solid Medium Growth and Isolation of Axenic Microcystis Strains (Cyanobacteria)." Applied and Environmental Microbiology, Vol. 55, No. 10 (October 1989): pp. 2569-2571. Retrieved Mar. 10, 2023. https://journals.asm.org/doi/pdf/10.1128/aem.55.10.2569-2571.1989.
8) Guillard, R. R. L. and Ryther, J. H. "Studies of marine planktonic diatoms. I. Cyclotella nana Hustedt, and Detonula confervacea (cleve) Gran." Canadian Journal of Microbiology, 8 (April 1962): pp. 229-239.
9) "F/2 MEDIA." Algae Research and Supply. 2023. Retrieved 4/7/2023. https://algaeresearchsupply.com/pages/f-2-media.
10) Allaguvatova, R. et al. "A simple method for the cultivation of algae *Chlorella vulgaris* Bejerinck." IOP Conference Series Earth and Environmental Science, 390 (November 2019).
11) "Specialty Agarose: Low Melt, High Res and 3:1 Grades." 2023. Retrieved 4/7/2023. https://www.benchmarkscientific.com/wp-content/uploads/2017/08/A1800-Specialty-Agarose-Brochure-HR-EM.pdf.
12) Deniz, I. "Determination of growth conditions for *Chlorella vulgaris*." Marine Science and Technology Bulletin, Vol. 9, No. 2 (2020): pp. 114-117.
13) Daliri, S. et al. "Investigation of optimal condition for *Chlorella vulgaris* microalgae growth." Global Journal of Environmental Science and Management (GJESM), Vol. 3, No. 2 (Spring 2017): pp. 217-230.
14) Serra-Mala, R. et al. "Influence of temperature on *Chlorella vulgaris* growth and mortality rates in a photobioreactor." Algal Research, 18 (2016): pp. 352-359.
15) Li, W. K. W. "Temperature Adaptation in Phytoplankton: Cellular and Photosynthetic Characteristics." Primary Productivity in the Sea, Springer, US (1980): pp. 259-279.
16) Cassidy, K. O. "THESIS: Evaluating Algal Growth at Different Temperatures, Biosystems and Agricultural Engineering." University of Kentucky, 2011.

What is claimed is:

1. A method for preparing a solid medium platform for cultivating algae, comprising:
  A) obtaining an algae culture solution ("AC S") at approximately room temperature or approximately 20° C. of a specific volumetric quantity, denoted "x";
  B) creating raw agarose solution ("AS") by adding low melting point agarose powder ("AP") to water of a volume equal to "x" in a container that is different from the one used for said ACS;
  C) heating and stirring AS until the mixture is homogeneous;
  D) cooling or waiting for the AS to cool down to approximately 15-35% above the gelling temperature of the AS;
  E) adding micronutrients supportive of algae growth after AS has cooled to approximately 15-35% above the gelling temperature of the AS to create an agarose micronutrient solution ("AMS");
  F) waiting for the AMS to cool to a temperature such that the simple average of the AMS and room temperature ACS are in the range of above the gelling temperature of the AMS at the lower end and 33° C. at the upper end;
  G) combining the AMS with ACS and pouring the mixture into a sufficiently large open container and stirring;
  H) apportioning the AMS/ACS mixture into cultivating container(s); and
  I) waiting for the mixture to congeal into algae in solid medium ("AiSM").

2. The method as recited in claim 1, wherein said AP has a melting temperature of less than or equal to 65° C. and a gelling temperature of 26-30° C.

3. The method as recited in claim 2, wherein said AS is created by mixing AP to water at a ratio of 1 gram AP per 50 mL water.

4. The method as recited in claim 1, wherein the heating and stirring of said AS are done in alternating stages, wherein the AS is heated, then heating is suspended, then the AS is stirred vigorously, then stirring is suspended and heating is resumed, wherein this process is alternately repeated until the agarose powder is no longer visible.

5. The method as recited in claim 4, wherein heating of said AS is accomplished using a 600-watt microwave for approximately 30 seconds.

6. The method as recited in claim 1, wherein said micronutrients comprise two separate components, wherein the first component denoted "A" comprises a nutrient solution and vitamin solution and the second component denote "B" comprises a trace metal solution.

7. The method as recited in claim 6, wherein said micronutrients are the F/2 trace metal solution or equivalent.

8. The method as recited in claim 7, wherein said AMS is created from said AS by adding micronutrient component "A" and micronutrient component "B" at a ratio of 1 mL of each micronutrient for every 2000 mL of AS.

9. The method as recited in claim 1, further comprising:
apportioning said AMS/ACS mixture into one or more cultivating container(s), each having an aspect ratio ("AR") of approximately 0.1 or less;
wherein if the container has a circular base, the AR is equal to the height of the container divided by the diameter of the circular base;
wherein if the container's base has an elliptical shape, the AR is equal to the height of the container divided by the average of the ellipse's major and minor axis dimensions;
wherein if the container's base has a square shape, the AR is equal to the height of the container divided by the base square's edge length;
wherein if the container's base has a straight-edged (faceted) shape with non-equilateral edges, the AR is equal to the height of the container divided by the average length of each edge in the base;
wherein the mixture's exposed surface area to volume ratio is higher than 100; and
wherein the height of the mixture in each container is at least 2 mm.

10. The method as recited in claim 1, further comprising apportioning said AMS/ACS mixture into cultivating container(s) at a height of 2-10 mm and a base container geometry set to achieve a mixture exposed surface area to volume ratio higher than 100.

* * * * *